United States Patent
Zimmerman et al.

(10) Patent No.: US 9,988,619 B2
(45) Date of Patent: Jun. 5, 2018

(54) NON-NATURAL AMINO ACID TRNA SYNTHETASES FOR PYRIDYL TETRAZINE

(71) Applicant: SUTRO BIOPHARMA, INC., South San Francisco, CA (US)

(72) Inventors: Erik S. Zimmerman, Pacifica, CA (US); Christopher Thanos, Tiburon, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 94 days.

(21) Appl. No.: 15/028,379

(22) PCT Filed: Oct. 10, 2014

(86) PCT No.: PCT/US2014/060061
§ 371 (c)(1),
(2) Date: Apr. 8, 2016

(87) PCT Pub. No.: WO2015/054590
PCT Pub. Date: Apr. 16, 2015

(65) Prior Publication Data
US 2016/0257945 A1  Sep. 8, 2016

Related U.S. Application Data

(60) Provisional application No. 61/890,033, filed on Oct. 11, 2013.

(51) Int. Cl.
*C07K 14/00* (2006.01)
*C07D 213/55* (2006.01)
*C12N 9/52* (2006.01)
*C12N 9/00* (2006.01)
*C12P 21/02* (2006.01)

(52) U.S. Cl.
CPC .............. *C12N 9/93* (2013.01); *C12P 21/02* (2013.01); *C12Y 601/01* (2013.01); *C12Y 601/01001* (2013.01)

(58) Field of Classification Search
CPC combination set(s) only.
See application file for complete search history.

(56) References Cited

U.S. PATENT DOCUMENTS 8,216,804 B2   7/2012  Schultz et al.

OTHER PUBLICATIONS

Schmidt et al ( A need for speed: Genetic encoding of rapid cycloaddition chemistries for protein labeling in living cells ChemBioChem 13(11), pp. 1553-1557), 2012.*
Seitchik et al (Genetically Encoded Tetrazine Amino Acid Directs Rapid Site-Specific in Vivo Bioorthogonal Ligation with trans-Cyclooctenes, J. Am. Chem. Soc. 2012, 134, 2898-2901.*
EP14851807.9 , "Extended European Search Report", dated Feb. 17, 2017, 4 pages.
PCT/US2014/060061, "Invitation to Pay Add'l Fees and Partial Search Rpt", dated Feb. 4, 2015, 2 pages.
"Tyrosyl-tRNA synthetase [Methanocaldococcus jannaschii]", NCBI Reference WP _010869888.1 , retrieved from the Internet: <http://www.ncbi.nlm.nih.gov/protein/WP_010869888.1>, May 15, 2013.
Schmidt, et al., "A Need for Speed: Genetic Encoding of Rapid Cycloaddition Chemistries for Protein Labelling in Living Cells", ChemBioChem, vol. 13, issue 11, 2012, pp. 1553-1557.
Seitchik, et al., "Genetically Encoded Tetrazine Amino Acid Directs Rapid Site-Specific in Vivo Bioorthogonal Ligation with trans-Cyclooctenes", Journal of the American Chemical Society, 134(6), Feb. 15, 2012, pp. 2898-2901.
PCT/US2014/060061, , "International Search Report and Written Opinion", dated Apr. 13, 2015, 12 pages.

* cited by examiner

*Primary Examiner* — Kagnew H Gebreyesus
(74) *Attorney, Agent, or Firm* — Kilpatrick Townsend & Stockton LLP

(57) ABSTRACT

The invention provides methods and compositions for a mutein aminoacyl-tRNA synthetase that preferentially charges a tRNA with a non-natural amino acid. Also provided are methods for incorporating the non-natural amino acids, pyridinyl-amino tetrazine amino acids, into a protein, and further conjugating a biologically active adduct to the pyridinyl-amino tetrazine.

10 Claims, 2 Drawing Sheets

NON-NATURAL AMINO ACID TRNA SYNTHETASES FOR PYRIDYL TETRAZINE

CROSS-REFERENCES TO RELATED APPLICATIONS

This application is a U.S. National Phase under 35 USC 371 of PCT Application No. PCT/US2014/060061, filed Oct. 10, 2014, which claims priority to U.S. Provisional Application No. 61/890,033, filed Oct. 11, 2013, the disclosures of which are hereby incorporated by reference in their entirety for all purposes.

REFERENCE TO A "SEQUENCE LISTING," A TABLE, OR A COMPUTER PROGRAM LISTING APPENDIX SUBMITTED ON A COMPACT DISK

This application includes a Sequence Listing as a text file named "Sequence Listing for 091200-1002967-006210US.txt" created Sep. 26, 2014, and containing 13,613 bytes. The material contained in this text file is incorporated by reference in its entirety for all purposes.

BACKGROUND OF THE INVENTION

Protein drug conjugates such as antibody drug conjugates (ADCs) are a targeted chemotherapeutic currently at the cutting edge of oncology medicine. ADCs, for example, consist of a tumor antigen-specific antibody that is coupled to a chemotherapeutic small molecule cytotoxin. Through targeted delivery of potent cytotoxins, protein drug conjugates exhibit improved therapeutic index over traditional chemotherapies with enhanced efficacy relative to standard monoclonal antibody therapies. However, current methods utilize nonspecific modes of conjugation of drugs to proteins, thereby leading to heterogeneous drug products with varied numbers of drugs conjugated across a number of possible sites. Technical challenges associated with drug conjugation to proteins using naturally occurring amino acids, are primarily due to heterogeneous degrees and location of drug loading as well as conjugate instability.

In order to reduce product heterogeneity, several groups have reported site-directed approaches that utilize substituted cysteines or enzymatic modification of engineered glutamine for conjugation. Site-specific ADCs have comparable potency to randomly conjugated ADCs while exhibiting superior therapeutic index and pharmacokinetics. However, limitations exist in thiol-based coupling stability due to plasma hydrolysis of the succinimde ring of the thiomaleimide conjugate, resulting in drug transfer to serum albumin. Furthermore, the partial reduction and reformation of disulfide bonds that facilitates conjugation to the engineered free cysteine, can lead to aberrant disulfide-mediated quaternary structure. An alternative to using introduced free cysteine residues is to use site-specific incorporation of non-natural amino acids with chemical side chains that are compatible with bio-orthogonal conjugation chemistry.

The essential componentry of any non-natural amino acid (nnAA) incorporation system consists of an aminoacyl tRNA synthetase (aaRS) that charges a specific tRNA with a nnAA. The aaRS-tRNA pair must be orthogonal with respect to the host cell or expression system in which they are employed. That is, the nnAA-specific synthetase must not recognize any host tRNAs or cognate amino acids, and the tRNA must not be aminoacylated by any host aaRS. Additionally, the orthogonal tRNA anticodon is often mutated to recognize a stop or nonsense codon. Repurposing of non-proteinogenic codons, such as the amber stop codon TAG, enables incorporation of a nnAA at any site in a protein through mutagenesis of the mRNA coding sequence to TAG. Amber suppression is the most widely used mode of co-translational, enzyme catalyzed nnAA incorporation. Non-natural amino acids with bio-orthogonal reactive chemical side chains can be used as a chemical "handle" to conjugate various payloads to discrete sites in a protein. This approach can generate additional functionality to proteins by direct conjugation of biologically active adduct, such as fluorescent or radioactive labels, photoactivatable markers, pharmacokinetic modifying PEGs, or chemotherapeutic agents. Unfortunately, the current methods for nnAA incorporation and conjugation of bio-orthogonal reactive chemical side chains into proteins are hindered by low overall product yield, nnAA incorporation inefficiency and low conjugation efficiency.

There is a need in the art for improved methods of site-specific incorporation of nnAAs and conjugation of biologically active adducts to proteins to form homogeneously conjugated protein drug conjugate therapeutics. The present invention satisfies these and other needs.

BRIEF SUMMARY OF THE INVENTION

In a first aspect, the present invention provides a composition comprising an aminoacyl-tRNA synthetase (RS) wherein the RS:

i) preferentially aminoacylates to a degree of greater than 90%, e.g., 91%, 92%, 93%, 94%, 95%, 96%, 97%, 98% or more a tRNA with (S)-2-amino-3-(5-(((6-methyl-1,2,4,5-tetrazin-3-ylamino)methyl)pyridin-2-yl)propanoic acid or a compound having the formula:

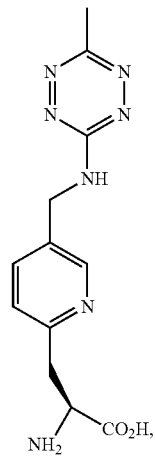

I compared to the 20 common naturally occurring amino acids;

ii) has a sequence identity of over 80%, e.g., 81%, 82%, 83%, 84%, 85%, 86%, 87%, 88%, 89%, 90%, 91%, 92%, 93%, 94%, 95%, 96%, 97%, 98% or more to *Methanococcus jannaschii* tyrosyl tRNA synthetase (TyrRS) having SEQ ID NO: 1; and iii) using SEQ ID NO: 1 as a reference sequence, has:
a) at position Y32 amino acid: L; b) at position L65 amino acid: V; c) at position H70 amino acid: A; d) at position F108 amino acid: W; e) at position Q109 amino acid: S; f) at position D158 amino acid: V; g) at position I159 amino acid A; and h) at position L162 amino acid: S or V.

In some embodiments, the composition further includes an amino acid substitution L162S. In other embodiments, the composition further includes an amino acid substitution L162V.

In some embodiments, the RS has a sequence identity of at least 90%, e.g., 90%, 91%, 92%, 93%, 94%, 95%, 96%, 97%, 98%, or more of SEQ ID NO:1. In another embodiment, the RS is selected from the group of amino acid sequences consisting of SEQ ID NO: 2 and SEQ ID NO: 3. The RS can have an amino acid sequence identity of at least 90%, e.g., 90%, 91%, 92%, 93%, 94%, 95%, 96%, 97%, 98% or more identity, to the wild-type *Methanococcus jannaschii* tyrosyl tRNA synthetase (TyrRS) sequence (SEQ ID NO:1).

In a second aspect, the present invention provides is a polynucleotide encoding an aminoacyl-tRNA synthetase (RS) wherein the RS:
i) preferentially aminoacylates to a degree of greater than 90%, e.g., 91%, 92%, 93%, 94%, 95%, 96%, 97%, 98%, 99%, or 100% a tRNA with (S)-2-amino-3-(5-((6-methyl-1,2,4,5-tetrazin-3-ylamino)methyl)pyridin-2-yl)propanoic acid or a compound of Formula I, compared to the 20 common naturally occurring amino acids;
ii) has a sequence identity of over 80%, e.g., 81%, 82%, 83%, 84%, 85%, 86%, 87%, 88%, 89%, 90%, 91%, 92%, 93%, 94%, 95%, 96%, 97%, 98% or more to *Methanococcus jannaschii* tyrosyl tRNA synthetase (TyrRS) having SEQ ID NO: 1; and
iii) using SEQ ID NO: 1 as a reference sequence, has:
a) at position Y32 amino acid: L; b) at position L65 amino acid: V; c) at position H70 amino acid: A; d) at position F108 amino acid: W; e) at position Q109 amino acid: S; f) at position D158 amino acid: V; g) at position I159 amino acid A; and h) at position L162 amino acid: S or V.

In some embodiments, the polynucleotide encodes the RS having the amino acid substitution L162S. In other embodiments, the polynucleotide encodes the RS having the amino acid substitution L162V.

In some embodiments, the RS is selected from the group of amino acid sequences consisting of SEQ ID NO: 2 and SEQ ID NO: 3.

In a third aspect, the present invention provides is a cell free protein synthesis system for selectively incorporating (S)-2-amino-3-(5-((6-methyl-1,2,4,5-tetrazin-3-ylamino)methyl)pyridin-2-yl)propanoic acid or a compound of Formula I into a protein of interest, the system comprising:
a) a cell free extract of bacteria having biologically functioning tRNA, amino acids and ribosomes necessary for cell free protein synthesis;
b) a polynucleotide having a coding region encoding the protein of interest and including a suppression codon selectively positioned within its coding region;
c) the compound of Formula I in a concentration sufficient to permit selective incorporation of the compound of Formula I into the protein of interest;
d) a tRNA able to be charged with the compound of Formula I and complementary to the suppression codon of the protein of interest; and
e) an aminoacyl-tRNA synthetase (RS) wherein the RS:
i) preferentially aminoacylates to a degree of greater than 90%, e.g., 91%, 92%, 93%, 94%, 95%, 96%, 97%, 98%, 99% or 100% a tRNA with the compound of Formula I compared to the 20 common naturally occurring amino acids;
ii) has a sequence identity of over 80%, e.g., 81%, 82%, 83%, 84%, 85%, 86%, 87%, 88%, 89%, 90%, 91%, 92%, 93%, 94%, 95%, 96%, 97%, 98% or more to *Methanococcus jannaschii* tyrosyl tRNA synthetase (TyrRS) having SEQ ID NO:1; and
iii) using SEQ ID NO: 1 as a reference sequence, has:
a) at position Y32 amino acid: L; b) at position L65 amino acid: V; c) at position H70 amino acid: A; d) at position F108 amino acid: W; e) at position Q109 amino acid: S; f) at position D158 amino acid: V; g) at position I159 amino acid A; and h) at position L162 amino acid: S or V.

In some embodiments, the RS of the cell free protein synthesis system has a sequence identity of at least 90%, e.g., 90%, 91%, 92%, 93%, 94%, 95%, 96%, 97%, 98% or more to the SEQ ID NO: 1. In some embodiments, the RS is selected from the group of amino acids sequences consisting of SEQ ID NO: 2 and SEQ ID NO: 3.

In some embodiments, the cell free extract has an active oxidative phosphorylation system. In some embodiments, the protein of interest is an antibody or antibody fragment.

In a fourth aspect, the present invention provides is a method for selectively incorporating (S)-2-amino-3-(5-(6-methyl-1,2,4,5-tetrazin-3-ylamino)pyridin-3-yl)propanoic acid or a compound of Formula I into a protein of interest, the method comprising the steps of:
a) combining a cell free extract of bacteria having containing biologically functioning tRNA, amino acids and ribosomes necessary for cell free protein synthesis with the following reagents:
i) a polynucleotide having a coding region encoding the protein of interest and including a suppression codon selectively positioned within its coding region;
ii) the compound of Formula I in a concentration sufficient to permit selective incorporation of the compound of Formula I into the protein of interest;
iii) a tRNA able to be charged with the compound of Formula I and complementary to the suppression codon of the target of interest; and
iv) an aminoacyl-tRNA synthetase (RS) wherein the RS: preferentially aminoacylates to a degree of greater than 90%, e.g., 91%, 92%, 93%, 94%, 95%, 96%, 97%, 98%, 99%, or 100% a tRNA with the compound of Formula I compared to the 20 common naturally occurring amino acids; has a sequence identity of over 80% to *Methanococcus jannaschii* tyrosyl tRNA synthetase (TyrRS) having SEQ ID NO: 1 (WT); and using SEQ ID NO: 1 as a reference sequence, has: a) at position Y32 amino acid: L; b) at position L65 amino acid: V; c) at position H70 amino acid: A; d) at position F108 amino acid: W; e) at position Q109 amino acid: S; f) at position D158 amino acid: V; g) at position I159 amino acid: A and h) at position L162 amino acid: S or V; and
b) incubating the combination of step (a) under conditions permitting selective incorporation of the compound of Formula I into the protein of interest.

In some embodiments, the RS of the method has the amino acid substitution L162S. In some embodiments, the RS has the amino acid substitution L162V.

In some embodiments, the RS has a sequence identity of at least 90%, e.g., 90%, 91%, 92%, 93%, 94%, 95%, 96%, 97%, 98% or more to SEQ ID NO: 1. In other embodiments, the RS is selected from the group of amino acid sequences consisting of SEQ ID NO: 2 and SEQ ID NO: 3.

In some embodiments, the cell free extract has an active oxidative phosphorylation system. In some embodiments, the protein of interest is an antibody or antibody fragment.

In some embodiments, the method further comprise the step of conjugating a biologically active adduct to the compound of Formula I within the protein of interest. In some instances, the conjugation is by a chemical reaction between a tetrazine of the protein of interest and a trans-cyclooctene on the biologically active adduct. In other instances, the conjugation is by a chemical reaction between a tetrazine of the protein of interest and a methylcyclopropene on the biologically active adduct.

In a fifth aspect, the present invention provides a composition comprising an aminoacyl-tRNA synthetase (RS) wherein the RS:
  i) preferentially aminoacylates to a degree of greater than 90%, e.g., 91%, 92%, 93%, 94%, 95%, 96%, 97%, 98%, 99%, or 100% a tRNA with (S)-2-amino-3-(5-(6-methyl-1,2,4,5-tetrazin-3-ylamino)pyridin-3-yl)propanoic acid or a compound having the formula:

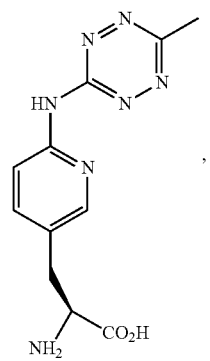

II compared to the 20 common naturally occurring amino acids;
  ii) has a sequence identity of over 80%, e.g., 81%, 82%, 83%, 84%, 85%, 86%, 87%, 88%, 89%, 90%, 91%, 92%, 93%, 94%, 95%, 96%, 97%, 98% or more to *Methanococcus jannaschii* tyrosyl tRNA synthetase (TyrRS) having SEQ ID NO:1; and
  iii) using SEQ ID NO: 1 as a reference sequence, has: a) at position Y32 amino acid: G; b) at position L65 amino acid: V or A; c) at position H70 amino acid: A or H; d) at position F108 amino acid: P or F or W; e) at position Q109 amino acid: Q or H or S; f) at position D158 amino acid: G; g) at position I159 amino acid A; and h) at position L162 amino acid: S or G.

In some embodiments, the RS of the method has the amino acid substitution L65A. some embodiments, the RS of the method has the amino acid substitution L65V. In some embodiments, the RS is selected from the group of amino acids sequences consisting of SEQ ID NO:4 and SEQ ID NO:5.

In some embodiments, the RS has a sequence identity of at least 90% of SEQ ID NO: 1. The RS can have an amino acid sequence identity of at least 90%, e.g., 90%, 91%, 92%, 93%, 94%, 95%, 96%, 97%, 98%, or more to the wild-type *Methanococcus jannaschii* tyrosyl tRNA synthetase (TyrRS) sequence (SEQ ID NO: 1).

In a sixth aspect, the present invention provides is a polynucleotide encoding an aminoacyl-tRNA synthetase (RS) wherein the RS:
  i) preferentially aminoacylates to a degree of greater than 90%, e.g., 91%, 92%, 93%, 94%, 95%, 96%, 97%, 98%, 99% or 100% a tRNA with (S)-2-amino-3-(5-(6-methyl-1,2,4,5-tetrazin-3-ylamino)pyridin-3-yl)propanoic acid or a compound of Formula II, compared to the 20 common naturally occurring amino acids;
  ii) has a sequence identity of over 80%, e.g., 81%, 82%, 83%, 84%, 85%, 86%, 87%, 88%, 89%, 90%, 91%, 92%, 93%, 94%, 95%, 96%, 97%, 98% or more to *Methanococcus jannaschii* tyrosyl tRNA synthetase (TyrRS) having SEQ ID NO: 1; and
  iii) using SEQ ID NO: 1 as a reference sequence, has: a) at position Y32 amino acid: G; b) at position L65 amino acid: V or A; c) at position H70 amino acid: A or H; d) at position F108 amino acid: P or F or W; e) at position Q109 amino acid: Q or H or S; f) at position D158 amino acid: G; g) at position I159 amino acid A; and h) at position L162 amino acid: S or G.

In some embodiments, the RS has a sequence identity of at least 90% of SEQ ID NO: 1, e.g., 90%, 91%, 92%, 93%, 94%, 95%, 96%, 97%, 98% or more to SEQ ID NO: 1. In some embodiments, the RS of the method has the amino acid substitution L65A. In some embodiments, the RS of the method has the amino acid substitution L65V.

In some embodiments, the RS is selected from the group of amino acid sequences consisting of SEQ ID NO: 4 and SEQ ID NO: 5.

In a seventh aspect, the present invention provides is a cell free protein synthesis system for selectively incorporating (S)-2-amino-3-(5-(6-methyl-1,2,4,5-tetrazin-3-ylamino) pyridin-3-yl)propanoic acid or a compound of Formula II into a protein of interest, the system comprising:
  a) a cell free extract of bacteria having biologically functioning tRNA, amino acids and ribosomes necessary for cell free protein synthesis;
  b) a polynucleotide having a coding region encoding the protein of interest and including a suppression codon selectively positioned within its coding region;
  c) the compound of Formula II in a concentration sufficient to permit selective incorporation of the compound of Formula II into the protein of interest;
  d) a tRNA able to be charged with the compound of Formula II and complementary to the suppression codon of the protein of interest; and
  e) an aminoacyl-tRNA synthetase (RS) wherein the RS:
    i) preferentially aminoacylates to a degree of greater than 90%, e.g., 91%, 92%, 93%, 94%, 95%, 96%, 97%, 98%, 99% or 100% a tRNA with the compound of Formula II compared to the 20 common naturally occurring amino acids;
    ii) has a sequence identity of over 80%, e.g., 81%, 82%, 83%, 84%, 85%, 86%, 87%, 88%, 89%, 90%, 91%, 92%, 93%, 94%, 95%, 96%, 97%, 98% or more to

*Methanococcus jannaschii* tyrosyl tRNA synthetase (TyrRS) having SEQ ID NO: 1; and iii) using SEQ ID NO:1 as a reference sequence, has: a) at position Y32 amino acid: G; b) at position L65 amino acid: V or A; c) at position H70 amino acid: A or H; d) at position F108 amino acid: P or F or W; e) at position Q109 amino acid: Q or H or S; f) at position D158 amino acid: G; g) at position I159 amino acid A; and h) at position L162 amino acid: S or G In some embodiments, the RS of the cell free protein synthesis system has a sequence identity of at least 90%, e.g., 90%, 91%, 92%, 93%, 94%, 95%, 96%, 97%, 98% or more of the SEQ ID NO: 1.

In some embodiments, the RS of the method has the amino acid substitution L65A. In some embodiments, the RS of the method has the amino acid substitution L65V. In some embodiments, the RS is selected from the group of amino acids sequences consisting of SEQ ID NO: 4 and SEQ ID NO: 5.

In some embodiments, the cell free extract has an active oxidative phosphorylation system. In some embodiments, the protein of interest is an antibody or antibody fragment.

In an eighth aspect, the present invention provides is a method for selectively incorporating (S)-2-amino-3-(5-(6-methyl-1,2,4,5-tetrazin-3-ylamino)pyridin-3-yl)propanoic acid or a compound of Formula II into a protein of interest, the method comprising the steps of:

a) combining a cell free extract of bacteria having containing biologically functioning tRNA, amino acids and ribosomes necessary for cell free protein synthesis with the following reagents:

i) a polynucleotide having a coding region encoding the protein of interest and including a suppression codon selectively positioned within its coding region;

ii) the compound of Formula II in a concentration sufficient to permit selective incorporation of the compound of Formula II into the protein of interest;

iii) a tRNA able to be charged with the compound of Formula II and complementary to the suppression codon of the target of interest; and iv) an aminoacyl-tRNA synthetase (RS) wherein the RS: preferentially aminoacylates to a degree of greater than 90%, e.g., 90%, 91%, 92%, 93%, 94%, 95%, 96%, 97%, 98%, 99% or 100% a tRNA with the compound of Formula II compared to the 20 common naturally occurring amino acids; has a sequence identity of over 80%, e.g., 81%, 82%, 83%, 84%, 85%, 86%, 87%, 88%, 89%, 90%, 91%, 92%, 93%, 94%, 95%, 96%, 97%, 98% or more to *Methanococcus jannaschii* tyrosyl tRNA synthetase (TyrRS) having SEQ ID NO: 1 (WT); and using SEQ ID NO:1 as a reference sequence, has: a) at position Y32 amino acid: G; b) at position L65 amino acid: V or A; c) at position H70 amino acid: A or H; d) at position F108 amino acid: P or F or W; e) at position Q109 amino acid: Q or H or S; f) at position D158 amino acid: G; g) at position I159 amino acid A; and h) at position L162 amino acid: S or G; and b) incubating the combination of step (a) under conditions permitting selective incorporation of the compound of Formula II into the protein of interest.

In some embodiments, the RS of the method has the amino acid substitution L65A. In some embodiments, the RS of the method has the amino acid substitution L65V.

In some embodiments, the RS has a sequence identity of at least 90%, e.g., 90%, 91%, 92%, 93%, 94%, 95%, 96%, 97%, 98% or more to SEQ ID NO: 1. In other embodiments, the RS is selected from the group of amino acid sequences consisting of SEQ ID NO: 4 and SEQ ID NO: 5

In some embodiments, the cell free extract has an active oxidative phosphorylation system. In some embodiments, the protein of interest is an antibody or antibody fragment.

In some embodiments, the method further comprise the step of conjugating a biologically active adduct to the compound of Formula II within the protein of interest. In some instances, the conjugation is by a chemical reaction between a tetrazine of the protein of interest and a trans-cyclooctene on the biologically active adduct. In other instances, the conjugation is by a chemical reaction between a tetrazine of the protein of interest and a methylcyclopropene on the biologically active adduct.

Other objects, features, and advantages of the present invention will be apparent to one of skill in the art from the following detailed description and figures.

DETAILED DESCRIPTION OF THE INVENTION

Figure 1:
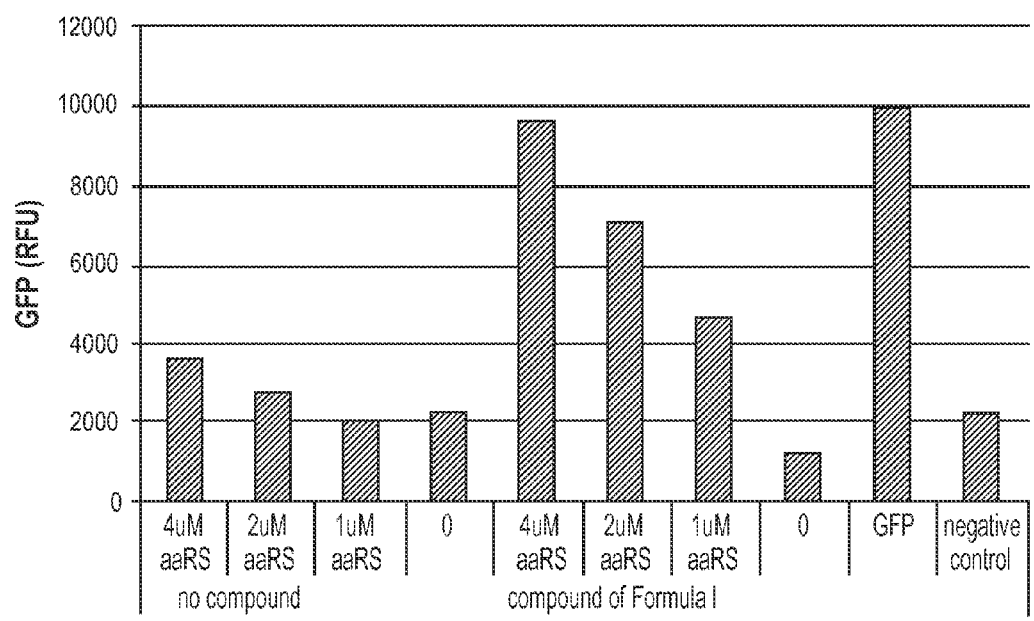
FIG. 1 shows GFP expression in the CFPS based GFP K49TAG amber suppression assay for the 2A2 variant which contains the following amino acid substitutions relative to SEQ ID NO:1: Y32L, L65V, H70A, F108W, Q109S, D158V, I159A and L162V. The assay measures GFP expression in the presence and absence of the non-natural amino acid of Formula I.

Provided herein are compositions and methods for the site-specific incorporation of the non-natural amino acids, (S)-2-amino-3-(5-((6-methyl-1,2,4,5-tetrazin-3-ylamino) methyl)pyridin-2-yl)propanoic acid (e.g., the compound Formula I) and (S)-2-amino-3-(5-(6-methyl-1,2,4,5-tetrazin-3-ylamino)pyridin-3-yl)propanoic acid (e.g., the compound Formula II), into proteins of interest using a cell-free synthesis system. In addition, provided herein is a composition of a variant of the *Methanococcus jannaschii* tyrosyl tRNA synthetase (TyrRS) having high activity and increased specificity for the compound of Formula I, compared to the common naturally occurring amino acids. Also, provided is a a composition of a variant of the *M. jannaschii* tTyrRS having high activity and increased specificity for the compound of Formula II, compared to the 20 natural amino acids.

I. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, NY 1989);

Ausubel et al., CURRENT PROTOCOLS IN MOLECULAR BIOLOGY, John Wiley and Sons (Hoboken, NY 1995).

As used herein the singular forms "a," "and," and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

The term "aminoacylation" or "aminoacylate" refers to the complete process in which a tRNA is charged with its correct amino acid that is a result of adding an aminoacyl group to a compound. As it pertains to this invention, a tRNA that undergoes aminoacylation or has been aminoacylated is one that has been charged with an amino acid, and an amino acid that undergoes aminoacylation or has been aminoacylated is one that has been charged to a tRNA molecule.

As used herein, the term "Formula I" refers to the compound (S)-2-amino-3-(5-((6-methyl-1,2,4,5-tetrazin-3-ylamino)methyl)pyridin-2-yl)propanoic acid which has the chemical structure of:

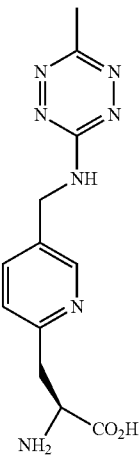 [SMILES: Cc1nnc(NCc2ccc(C[C@H](N)C(=O)O)nc2)nn1]

As used herein, the term "Formula II" refers to the compound (S)-2-amino-3-(5-(6-methyl-1,2,4,5-tetrazin-3-ylamino)pyridin-3-yl)propanoic acid which has the chemical structure of:

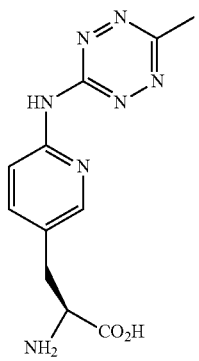 [SMILES: Cc1nnc(Nc2ccc(C[C@H](N)C(=O)O)cn2)nn1]

The term "aminoacyl-tRNA synthetase" or "tRNA synthetase" or "synthetase" or "aaRS" or "RS" refers to an enzyme that catalyzes a covalent linkage between an amino acid and a tRNA molecule. This results in an aminoacylated tRNA molecule, which is a tRNA molecule that has its respective amino acid attached via an ester bond.

The term "charged" in the context of tRNA refers to a the aminoacylation of a tRNA with an amino acid, both natural and non-natural, where the aminoacylation permits a ribosome to incorporate the amino acid into a polypeptide being translated from mRNA.

The term "biologically active adduct" refers to a chemical, molecule or reagent that can perform a function in a cell or an organism. For example, the function may include cell proliferation, apoptosis, post-translational modification (e.g., phosphorylation), cell signaling activation, cell signaling inactivation, cell death, cell labeling, etc.

The term "selective incorporating" in the context of protein translation refers to including or introducing a specific amino acid (e.g., a specific non-natural amino acid) in a predetermined, desired amino acid position in the sequence of the protein without disturbing the desired function of the protein.

The phrase "concentration sufficient to permit selective incorporation" refers to a minimal concentration of a component (e.g., RS, non-natural amino acid, amber suppressor tRNA) needed for the site-specific incorporation of the non-natural amino acid to a protein of interest.

The term "preferentially aminoacylates" refers to the preference of a tRNA synthtase to aminoacylate (charge) a particular tRNA molecule with a predetermined amino acid molecule compared to another amino acid molecule. In other words, the tRNA synthtase can selectively aminoacylate a non-natural amino acid (nnAA) over a naturally occurring amino acid. For example, the tRNA synthtase can aminoacylate a specific nnAA at a frequency greater of than 90%, e.g., 91%, 92%, 93%, 94%, 95%, 96%, 97%, 98%, 99%, or 100%, compared to any or all other natural amino acids.

The term "naturally occurring amino acid" or "natural amino acid" refers to any one of the 20 amino acids encoded by the genetic code, such as, (arginine, Arg, R; histidine, His, H; lysine, Lys, K; aspartic acid, Asp, D; glutamic acid, Glu, E; serine, S, Ser; threonine, Thr, T; asparagine, Asn, N; glutamine, Gln, Q; cysteine, Cys, G; glycine, Gly, G; proline, Pro, P; alanine, Ala, A; isoleucine, Ile, I; leucine, Leu, L; methionine, Met, M; phenylalanine; Phe, F; tryptophan, Trp, W; tyrosine, Tyr, Y, and valine, Val, V, that are precursors to proteins.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid or polynucleotide is used interchangeably with gene, cDNA, and mRNA encoded by a gene.

The term "peptide," "protein," and "polypeptide" are used herein interchangeably and refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins and truncated proteins, wherein the amino acid residues are linked by covalent peptide bonds.

The term "mutein" refers to a protein having an amino acid substitution relative to a wild-type or reference amino acid sequence.

The term "sequence identity" or "percent identity" in the context of two or more nucleic acids or polypeptide sequences, refers to two or more sequences that are the same or have a specified percentage of amino acid residues or nucleotides that are the same, when compared and aligned for maximum correspondence over a comparison window, as measured using a sequence comparison algorithm, e.g., BLASTP. For purposes of this document, the percent identity is determined over the full-length wild-type sequence such as the reference sequence set forth in SEQ ID NO:1. The method for calculating the sequence identity as provided herein is the BLASTP program having its defaults set at a wordlength (W) of 3, an expectation (E) of 10, and the BLOSUM62 scoring matrix (see, e.g., Henikoff and Henikoff, 1989, *Proc Natl Acad Sci* USA 89:10915). Exemplary determination of sequence alignment and % sequence identity can employ the BESTFIT or GAP programs in the GCG Wisconsin Software package (Accelrys, Madison Wis.), using default parameters provided.

The term "substitution at amino acid position" refers to a change of an amino acid residue at a specific position of the amino acid sequence of a protein. For example, the term "X20Y" refers to the substitution of the wild-type (reference) amino acid X at position 20 of the protein for amino acid Y.

The term "suppression codon" refers to a nucleotide triplet that is introduced into a polynucleotide at a predetermined location and is recognized by a specific tRNA that can recognize a stop codon (e.g., an amber, ochre or opal stop codon) and allows translation to read through the codon to produce the protein, thereby suppressing the introduced stop codon.

The term "biologically active protein" refers to a protein that retains at least some of the biological activity of the protein of interest. The biological activity can be determined by comparing the activity, function and/or structure of the protein of interest expressed by the methods described herein to the activity of a reference protein of interest. For example, if the reference protein of interest is an IgG, a biologically active protein will comprise a properly folded and assembled IgG molecule. In some embodiments, the reference protein can be a protein expressed by a bacterial cell free synthesis system that does not contain an exogenous protein chaperone. The biological activity can be determined using an in vitro or in vivo assay that is appropriate for the protein of interest. The biological activity of the protein of interest can be expressed as the biological activity per unit volume of the cell-free protein synthesis reaction mixture. In some embodiments, the biological activity of a protein produced by the methods described herein is at least 30%, 40%, 50%, 60%, 70%, 80%, 90%, 95% or 99% of the activity of a reference protein.

The term "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH—CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies also include single chain antibodies (antibodies that exist as a single polypeptide chain), and single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv); however, alternative expression strategies have also been successful. For example, Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see, e.g., U.S. Pat. Nos. 5,091,513, 5,132,405, and 4,956,778). Antibodies also include all those that have been displayed on phage (e.g., scFv, Fv, Fab and disulfide linked Fv (Reiter et al. (1995) Protein Eng. 8: 1323-1331). Antibodies can also include diantibodies, miniantibodies and scFv-Fc fusions.

As used herein, the term "Fab fragment" is an antibody fragment that contains the portion of the full-length antibody that results from digestion of a full-length immunoglobulin with papain, or a fragment having the same structure that is produced synthetically, e.g. recombinantly. A Fab fragment contains a light chain (containing a variable ($V_L$) and constant ($C_L$ region domain) and another chain containing a variable domain of a heavy chain ($V_H$) and one constant region domain portion of the heavy chain ($C_{H1}$).

As used herein, a F(ab')$_2$ fragment is an antibody fragment that results from digestion of an immunoglobulin with pepsin at pH 4.0-4.5, or a synthetically, e.g. recombinantly, produced antibody having the same structure. The F(ab')$_2$ fragment contains two Fab fragments but where each heavy chain portion contains an additional few amino acids, including cysteine residues that form disulfide linkages joining the two fragments.

The term "bacterial derived cell free extract" refers to preparation of in vitro reaction mixtures able to transcribe DNA into mRNA and/or translate mRNA into polypeptides. The mixtures include ribosomes, ATP, amino acids, and tRNAs. They may be derived directly from lysed bacteria, from purified components or combinations of both.

The term "cell-free synthesis" or "CFPS" refers to the in vitro synthesis of polypeptides in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc.; and co-factors, enzymes and other reagents that are necessary for the synthesis, e.g. ribosomes, uncharged tRNAs, tRNAs charged with unnatural amino acids, polymerases, transcriptional factors, tRNA synthetases, etc.

The term "active oxidative phosphorylation system" refers to a bacterial lysate that exhibits active oxidative phosphorylation during protein synthesis. For example, the bacterial lysate can generate ATP using ATP synthase enzymes and reduction of oxygen. It will be understood that other translation systems known in the art can also use an active oxidative phosphorylation during protein synthesis. The activation of oxidative phosphorylation can be demonstrated by inhibition of the pathway using specific inhibitors, such as electron transport chain inhibitors.

II. Detailed Description of Embodiments

Provided herein are compositions of and methods of producing a RS variant containing amino acid substitutions to wild-type *M. jannaschii* tyrosyl tRNA synthetase as set forth in SEQ ID NO: 1. The RS variants have high activity and increased specificity for the non-natural amino acid pyridinyl-amino tetrazine (e.g., Formula I or Formula II), compared to the common naturally occurring amino acids. Provided also are methods of introducing a suppressor codon into a polynucleotide encoding a protein of interest, such that the non-natural amino acid (e.g., (S)-2-amino-3-(5-((6-methyl-1,2,4,5-tetrazin-3-ylamino)methyl)pyridin-2-yl)propanoic acid or (S)-2-amino-3-(5-(6-methyl-1,2,4,5-tetrazin-3-ylamino)pyridin-3-yl)propanoic acid) is incorporated into a selected location in the protein of interest. In addition, methods for producing said protein of interest in a cell free protein synthesis system are described. Furthermore, methods for conjugating a biologically active adduct to the protein of interest via the non-natural amino acid are provided. Exemplary embodiments of producing pyridinyl-amino tetrazine-specific RS variants and a target protein with pyridinyl-amino tetrazine at a desired location are found in the Example.

A. General Methods

Unless defined otherwise, all technical and scientific terms used herein have the meaning commonly understood by one of ordinary skill in the art to which this invention belongs. Practitioners are particularly directed to Green, M. R., and Sambrook, J., eds., MOLECULAR CLONING: A LABORATORY MANUAL, 4th ed., Cold Spring Harbor Laboratory Press, Cold Spring Harbor, N.Y. (2012), and Ausubel, F. M., et al., CURRENT PROTOCOLS IN MOLECULAR BIOLOGY (SUPPLEMENT 99), John Wiley & Sons, New York (2012), which are incorporated herein by reference, for definitions and terms of the art. Standard methods also appear in Bindereif, Schön, & Westhof (2005) HANDBOOK OF RNA BIOCHEMISTRY, Wiley-VCH, Weinheim, Germany which describes detailed methods for RNA manipulation and analysis, and is incorporated herein by reference. Examples of appropriate molecular techniques for generating recombinant nucleic acids, and instructions sufficient to direct persons of skill through many cloning exercises are found in Green, M. R., and Sambrook, J., (Id.); Ausubel, F. M., et al., (Id.); Berger and Kimmel, GUIDE TO MOLECULAR CLONING TECHNIQUES, METHODS IN ENZYMOLOGY (Volume 152 Academic Press, Inc., San Diego, Calif. 1987); and PCR PROTOCOLS: A GUIDE TO METHODS AND APPLICATIONS (Academic Press, San Diego, Calif. 1990), which are incorporated by reference herein.

Methods for protein purification, chromatography, electrophoresis, centrifugation, and crystallization are described in Coligan et al. (2000) CURRENT PROTOCOLS IN PROTEIN SCIENCE, VOL. 1, John Wiley and Sons, Inc., New York. Methods for cell-free synthesis are described in Spirin & Swartz (2008) CELL-FREE PROTEIN SYNTHESIS, Wiley-VCH, Weinheim, Germany. Methods for incorporation of non-natural amino acids into proteins using cell-free synthesis are described in Shimizu et at (2006) FEBS Journal, 273, 4133-4140.

PCR amplification methods are well known in the art and are described, for example, in Innis et al., PCR Protocols: A Guide to Methods and Applications, Academic Press Inc. San Diego, Calif., 1990. An amplification reaction typically includes the DNA that is to be amplified, a thermostable DNA polymerase, two oligonucleotide primers, deoxynucleotide triphosphates (dNTPs), reaction buffer and magnesium. Typically a desirable number of thermal cycles is between 1 and 25. Methods for primer design and optimization of PCR conditions are well known in the art and can be found in standard molecular biology texts such as Ausubel et al., SHORT PROTOCOLS IN MOLECULAR BIOLOGY, 5th Edition, Wiley, 2002, and Innis et al., PCR PROTOCOLS, Academic Press, 1990. Computer programs are useful in the design of primers with the required specificity and optimal amplification properties (e.g., Oligo Version 5.0 (National Biosciences)). In some embodiments, the PCR primers may additionally contain recognition sites for restriction endonucleases, to facilitate insertion of the amplified DNA fragment into specific restriction enzyme sites in a vector. If restriction sites are to be added to the 5' end of the PCR primers, it is preferable to include a few (e.g., two or three) extra 5' bases to allow more efficient cleavage by the enzyme. In some embodiments, the PCR primers may also contain an RNA polymerase promoter site, such as T7 or SP6, to allow for subsequent in vitro transcription. Methods for in vitro transcription are well known to those of skill in the art (see, e.g., Van Gelder et al., *Proc. Natl. Acad. Sci. U.S.A.*, 87:1663-1667, 1990; Eberwine et al., *Proc. Natl. Acad. Sci. U.S.A.*, 89:3010-3014, 1992).

B. Introducing Amino Acid Substitutions to Wild-Type Aminoacyl-tRNA Synthetase.

Surprisingly, it has been determined that specific amino acid substitiutions within wild-type *M. jannaschii* tyrosyl tRNA synthetase (TyrRS) allow it to preferentially or selectively incorporate pyridinyl-amino tetrazine amino acids (e.g., (S)-2-amino-3-(5-((6-methyl-1,2,4,5-tetrazin-3-ylamino)methyl)pyridin-2-yl)propanoic acid or (S)-2-amino-3-(5-(6-methyl-1,2,4,5-tetrazin-3-ylamino)pyridin-3-yl)propanoic acid), but not any of the common naturally occurring amino acids. In addition, the synthetases do not aminoacylate any endogenous *E. coli* tRNAs with tyrosine, but can aminoacylate a mutant amber suppressor tRNA. The RS variant is generated from a wild-type TyrRS DNA sequence or the portion thereof containing the open reading frame, with changes made as required at the codons corresponding to substitutions described herein. In particular, the amino acid substitutions such as Y32L, L65V, H70A, F108W, Q109S, D158V, I159A, and L162S or L162Vcan be made by mutating the coding sequence of the wild-type *M. jannaschii* tTyrRS as set forth in SEQ ID NO: 1 to generate an RS variant specific for Formula I. The amino acid substitutions such as Y32G, L65V or L65A, H70A or H70V, F108P or F108W, Q109H or Q109S, D158G, I159A, L162G or L162S, or combinations thereof can be made by mutating the coding sequence of the wild-type *M. jannaschii* TyrRS as set forth in SEQ ID NO: 1 to generate an RS variant specific for Formula II.

The amino acid sequence of a specific RS variant provides a description of all polynucleotides capable of encoding the RS variant because of the known correspondence between amino acids and the genetic code. For most organisms the genetic code is "Amino Acid (one letter code) [codons]": phenylalanine (F) [TTT, TTC]; leucine (L) [TTA, TTG, CTT, CTC, CTA, CTG]; isoleucine (I) [ATT, ATC, ATA]; methionine (M) [ATG]; valine (V) [TGG, GTC, GTA, GTG]; serine (S) [TCT, TCC, TCA, TCG, AGT, AGC]; proline (P) [CCT, CCC, CCA, CCG]; threonine (T) [ACT, ACC, ACA, ACG]; alanine (A) [GCT, GCC, GCA, GCG]; tyrosine (Y) [TAT, TAC]; histidine (H) [CAT, CAC]; glutamine (Q) [CAA, CAG]; asparagine (N) [AAT, AAC]; lysine (K) AAA, AAG]; aspartic acid (D) [GAT, GAC]; glutamic acid (E) [GAA, GAG]; cysteine (C) [TGT, TGC]; tryptophan (W) [TGG]; arginine (R) [CGT, CGC, CGA, CGG, AGA, AGG]; and glycine (G) [GGT, GGC, GGA, GGG].

In some instances, the amino acid sequence can differ in one or more amino acids from those of the RS proteins provided herein as a result of one or more of the well-known conservative amino acids substitutions. Conservative substitutions for an amino acid within the RS protein sequence provided herein can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

For example, RS variants provided herein can contain conservative amino acid substitutions, such as, but not limited to, a RS variant with the following amino acid substitutions:

i) M6L, Y32L, L65V, H70A, F108W, Q109S, D158V, I159A, and L162S;

ii) M6L, L65V, H70A, F108W, Q109S, D158V, I159A, L162S, and L162V;

iii) M6L, Y32G, L65A, H70A, Q109S, D158G, and L162S;

iv) M6L, Y32G, L65V, H70A, Q109S, D158G, and L162S;

v) N10Q, Y32L, L65V, H70A, F108W, Q109S, D158V, I159A, and L162S;

vi) N10Q, L65V, H70A, F108W, Q109S, D158V, I159A, L162S, and L162V;

vii) N10Q, Y32G, L65A, H70A, Q109S, D158G, and L162S;

viii) N10Q, Y32G, L65V, H70A, Q109S, D158G, and L162S;

ix) I14L, Y32L, L65V, H70A, F108W, Q109S, D158V, I159A, and L162S;

x) I14L, L65V, H70A, F108W, Q109S, D158V, I159A, L162S, and L162V;

xi) I14L, Y32G, L65A, H70A, Q109S, D158G, and L162S;

xii) I14L, Y32G, L65V, H70A, Q109S, D158G, and L162S;

xiii) S16T, Y32L, L65V, H70A, F108W, Q109S, D158V, I159A, and L162S;

xiv) S16T, L65V, H70A, F108W, Q109S, D158V, I159A, L162S, and L162V;

xv) S16T, Y32G, L65A, H70A, Q109S, D158G, and L162S;

xvi) S16T, Y32G, L65V, H70A, Q109S, D158G, and L162S; and the like.

In some embodiments, the RS variant that preferentially aminoacetylates a tRNA with a compound of Formula I has a sequence identity of greater than 80% to SEQ ID NO:1 and the following amino acid substitutions: Y32L, L65V, H70A, F108W, Q109S, D158V, I159A, and L192S. Alternatively, the RS variant that preferentially aminoacetylates a tRNA with a compound of Formula I has a sequence identity of greater than 80% to SEQ ID NO:1 and the following amino acid substitutions: Y32L, L65V, H70A, F108W, Q109S, D158V, I159A, and L192V.

In some embodiments, the RS variant that preferentially aminoacetylates a tRNA with a compound of Formula II has a sequence identity of greater than 80% to SEQ ID NO:1 and the following amino acid substitutions: Y32L, D158G, I159A, L65V, H70A, F108P, Q109Q, L162S; Y32L, D158G, I159A, L65A, H70A, F108P, Q109Q, L162S; Y32L, D158G, I159A, L65V, H70H, F108P, Q109Q, L162S; Y32L, D158G, I159A, L65A, H70H, F108P, Q109Q, L162S; Y32L, D158G, I159A, L65V, H70A, F108F, Q109Q, L162S; Y32L, D158G, I159A, L65A, H70A, F108F, Q109Q, L162S; Y32L, D158G, I159A, L65V, H70H, F108F, Q109Q, L162S; Y32L, D158G, I159A, L65A, H70H, F108F, Q109Q, L162S; Y32L, D158G, I159A, L65V, H70A, F108W, Q109Q, L162S; Y32L, D158G, I159A, L65A, H70A, F108W, Q109Q, L162S; Y32L, D158G, I159A, L65V, H70H, F108W, Q109Q, L162S; Y32L, D158G, I159A, L65A, H70H, F108W, Q109Q, L162S; Y32L, D158G, I159A, L65V, H70A, F108P, Q109H, L162S; Y32L, D158G, I159A, L65A, H70A, F108P, Q109H, L162S; Y32L, D158G, I159A, L65V, H70H, F108P, Q109H, L162S; Y32L, D158G, I159A, L65A, H70H, F108P, Q109H, L162S; Y32L, D158G, I159A, L65V, H70A, F108F, Q109H, L162S; Y32L, D158G, I159A, L65A, H70A, F108F, Q109H, L162S; Y32L, D158G, I159A, L65V, H70H, F108F, Q109H, L162S; Y32L, D158G, I159A, L65A, H70H, F108F, Q109H, L162S; Y32L, D158G, I159A, L65V, H70A, F108W, Q109H, L162S; Y32L, D158G, I159A, L65A, H70A, F108W, Q109H, L162S; Y32L, D158G, I159A, L65V, H70H, F108W, Q109H, L162S; Y32L, D158G, I159A, L65A, H70H, F108W, Q109H, L162S; Y32L, D158G, I159A, L65V, H70A, F108P, Q109S, L162S; Y32L, D158G, I159A, L65A, H70A, F108P, Q109S, L162S; Y32L, D158G, I159A, L65V, H70H, F108P, Q109S, L162S; Y32L, D158G, I159A, L65A, H70H, F108P, Q109S, L162S; Y32L, D158G, I159A, L65V, H70A, F108F, Q109S, L162S; Y32L, D158G, I159A, L65A, H70A, F108F, Q109S, L162S; Y32L, D158G, I159A, L65V, H70H, F108F, Q109S, L162S; Y32L, D158G, I159A, L65A, H70H, F108F, Q109S, L162S; Y32L, D158G, I159A, L65V, H70A, F108W, Q109S, L162S; Y32L, D158G, I159A, L65A, H70A, F108W, Q109S, L162S; Y32L, D158G, I159A, L65V, H70H, F108W, Q109S, L162S; Y32L, D158G, I159A, L65A, H70H, F108W, Q109S, L162S; Y32L, D158G, I159A, L65V, H70A, F108P, Q109Q, L162G; Y32L, D158G, I159A, L65A, H70A, F108P, Q109Q, L162G; Y32L, D158G, I159A, L65V, H70H, F108P, Q109Q, L162G; Y32L, D158G, I159A, L65A, H70H, F108P, Q109Q, L162G; Y32L, D158G, I159A, L65V, H70A, F108F, Q109Q, L162G; Y32L, D158G, I159A, L65A, H70A, F108F, Q109Q, L162G; Y32L, D158G, I159A, L65V, H70H, F108F, Q109Q, L162G; Y32L, D158G, I159A, L65A, H70H, F108F, Q109Q, L162G; Y32L, D158G, I159A, L65V, H70A, F108W, Q109Q, L162G; Y32L, D158G, I159A, L65A, H70A, F108W, Q109Q, L162G; Y32L, D158G, I159A, L65V, H70H, F108W, Q109Q, L162G; Y32L, D158G, I159A, L65A, H70H, F108W, Q109Q, L162G; Y32L, D158G, I159A, L65V, H70A, F108P, Q109H, L162G; Y32L, D158G, I159A, L65A, H70A, F108P, Q109H, L162G; Y32L, D158G, I159A, L65V, H70H, F108P, Q109H, L162G; Y32L, D158G, I159A, L65A, H70H, F108P, Q109H, L162G; Y32L, D158G, I159A, L65V, H70A, F108F, Q109H, L162G; Y32L, D158G, I159A, L65A, H70A, F108F, Q109H, L162G; Y32L, D158G, I159A, L65V, H70H, F108F, Q109H, L162G; Y32L, D158G, I159A, L65A, H70H, F108F, Q109H, L162G; Y32L, D158G, I159A, L65V, H70A, F108W, Q109H, L162G; Y32L, D158G, I159A, L65A, H70A, F108W, Q109H, L162G; Y32L, D158G, I159A, L65V, H70H, F108W, Q109H, L162G; Y32L, D158G, I159A, L65A, H70H, F108W, Q109H, L162G; Y32L, D158G, I159A, L65V, H70A, F108P, Q109S, L162G; Y32L, D158G, I159A, L65A, H70A, F108P, Q109S, L162G; Y32L, D158G, I159A, L65V, H70H, F108P, Q109S, L162G; Y32L, D158G, I159A, L65A, H70H, F108P, Q109S, L162G; Y32L, D158G, I159A, L65V, H70A, F108F, Q109S, L162G; Y32L, D158G, I159A, L65A, H70A, F108F, Q109S, L162G; Y32L, D158G, I159A, L65V, H70H, F108F, Q109S, L162G; Y32L, D158G, I159A, L65A, H70H, F108F, Q109S, L162G; Y32L, D158G, I159A, L65V, H70A, F108W, Q109S, L162G; Y32L, D158G, I159A, L65A, H70A, F108W, Q109S, L162G; Y32L, D158G, I159A, 65V, H70H, F108W, Q109S, L162G; or Y32L, D158G, I159A, L65A, H70H, F108W, Q109S, L162G.

The RS variants of this invention are further defined by their ability to bind to polyclonal antibodies generated against the wild-type TyrRS having SEQ ID NO: 1. Under designated immunoassay conditions, the RS variants of this invention include those defined by their function, i.e., their ability selectively incorporate the non-natural amino acid and by their ability to also bind to the specified polyclonal antibodies at a rate of at least two times above the background. Typically a specific or selective reaction will be at least twice background signal or noise and more typically more than 10 to 100 times background. A variety of immunoassay formats may be used to determine if the test polyclonal antibodies react with an aaRS of this invention. See, e.g., Harlow & Lane, Antibodies, A Laboratory Manual (1988) for a description of immunoassay formats and conditions that can be used to determine specific immunoreactivity.

Methods for generate a coding sequence encoding a RS variant with amino acid substitutions include standard molecular cloning techniques such as, but not limited to, PCR, mutagenesis, and restriction enzyme cloning. Optionally, the coding sequence of RS variants can be produced using synthetic chemistry according to standard methods, e.g., the solid phase phosphoramidite triester method.

It is recognized by those skilled in the art that various well-known mutagenesis techniquesare available to generate the RS variants of this invention. For instance, point mutations corresponding to the desired amino acid substitutions described herein can be introduced to the coding sequence for wild-type *M. jannaschii* tyrosyl tRNA synthetase by overlapping PCR. Optionally, the wild-type coding sequence can be mutated using a PCR-based mutagenesis technique, e.g., site-directed mutagenesis, to mutate the codons corresponding to the desired amino acid substitutions of the RS variants. The desired polynucleotide encoding the RS variant is used to generate the RS variant protein.

More specifically such mutagenesis techniques include, e.g., site-directed mutagenesis (e.g., QuikchangeII™ Site Directed Mutagenesis kit, Agilent Technologies), random mutagenesis (Diversify™ PCR Random Mutagenesis Kit, Clontech), homologous recombinations, oligonucleotide-directed mutagenesis (e.g., Transformer™ Kit, Clontech), phosphorothioate-modified DNA mutagenesis, etc., can be used to generate a coding sequence corresponding to amino acid substitutions. See, e.g., Ling, et al., "Approaches to DNA mutagenesis: an overview," Anal. Biochem., 254(2): 157-78 (1997); Dale, et al., "Oligonucleotide-directed random mutagenesis using the phosphorothioate method," Methods Mol. Biol., 57:369-74 (1996); Smith, "In vitro mutagenesis," Ann. Rev. Genet., 19:423-462 (1985); Botstein, et al., "Strategies and applications of in vitro mutagenesis," Science, 229:1193-1201 (1985); Carter, "Site-directed mutagenesis," Biochem. J., 237:1-7 (1986); Kramer, et al., "Point Mismatch Repair," Cell, 38:879-887 (1984); Wells, et al., "Cassette mutagenesis: an efficient method for generation of multiple mutations at defined sites," Gene, 34:315-323 (1985); Minshull, et al., "Protein evolution by molecular breeding," Current Opinion in Chemical Biology, 3:284-290 (1999); Christians, et al., "Directed evolution of thymidine kinase for AZT phosphorylation using DNA family shuffling," Nature Biotechnology, 17:259-264 (1999); Crameri, et al., "DNA shuffling of a family of genes from diverse species accelerates directed evolution," Nature, 391:288-291; Crameri, et al., "Molecular evolution of an arsenate detoxification pathway by DNA shuffling," Nature Biotechnology, 15:436-438 (1997); Zhang, et al., "Directed evolution of an effective fucosidase from a galactosidase by DNA shuffling and screening," Proceedings of the National Academy of Sciences, U.S.A., 94:45-4-4509; Crameri, et al., "Improved green fluorescent protein by molecular evolution using DNA shuffling," Nature Biotechnology, 14:315-319 (1996); Stemmer, "Rapid evolution of a protein in vitro by DNA shuffling," Nature, 370:389-391 (1994); Stemmer, "DNA shuffling by random fragmentation and reassembly: In vitro recombination," Proceedings of the National Academy of Sciences, U.S.A., 91:10747-10751 (1994); WO 95/22625; WO 97/0078; WO 97/35966; WO 98/27230; WO 00/42651; WO 01/75767; and WO 2009/152336, all of which are incorporated herein by reference.

For instance, point mutations corresponding to the desired amino acid substitutions described herein can be introduced to the coding sequence for wild-type M. jannaschii TyrRS by overlapping PCR. Optionally, the wild-type coding sequence can be mutated using a PCR-based mutagenesis technique, e.g., site-directed mutagenesis, to mutate the codons corresponding to the desired amino acid substitutions of the RS variants. The desired polynucleotide encoding the RS variant is used to generate the RS variant protein.

C. Expressing Aminoacyl-tRNA Synthetases Specific for a Specific Pyridinyl-Amino Tetrazine.

Once the desired RS variant polynucleotide is obtained, it can be used to generate the corresponding polypeptide in a cell-based or a cell free expression system.

In a cell-based protein synthesis system, the polynucleotide encoding the RS variant is cloned into an expression vector such as a plasmid, phage, phagemid, cosmid, bacteriophage, baculovirus vector, yeast plasmid, and the like. The expression vector can include the nucleic acid of the present invention that is operably linked to a promoter. Subsequently, the expression vector is introduced into a host cell to express the RS variant. Any other vector may be used as long as it is replicable and viable in the host cell. The host cell can be a bacterial cell, an archaeal cell, a fungal cell, a yeast cell, an insect cell, or a mammalian cell. The RS variant can be produced in a cell and then purified from the cell lysate.

In a cell-free protein synthesis (CFPS) system, the polynucleotide encoding the RS variant serves as the polynucleotide template for the reaction. Other components of the reaction include one or more bacterial extracts and/or defined reagents. The reaction mix can also include at least ATP or an energy source, co-factors, enzymes and other reagents that are necessary for polypeptide synthesis, e.g., ribosomes, tRNA, polymerases, transcriptional factors, aminoacyl synthetases, elongation factors, initiation factors, etc. Further description of exemplary CFPS reaction systems are described below.

The RS variant protein can be purified following protein synthesis according to standard methods known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., PROTEIN PURIFICATION, J.-C. Janson and Lars Ryden, editors, VCH Publishers, New York, 1989) to obtain substantially pure polypeptides.

The activity and selectivity of the RS variant to charge the suppressor tRNA with the non-natural amino acid can be determined by using a reporter gene containing a suppressor codon. The activity of the RS variant in the presence of the pyridinyl-amino tetrazine compared to the 20 common naturally occurring amino acids can be measured by detecting the presence or absence of the reporter protein. A description of methods for introducing a suppressor codon into a polynucleotide encoding a target protein such as a reporter protein is provided in Example 2.

A positive selection reporter (e.g., a fluorescent reporter, luminescent reporter, or affinity-based reporter) can be used such that codon suppression results in a detectable, positive signal. For example, an amber codon can be introduced into the reporter gene (e.g., GFP gene). If the RS variant is able to charge the suppressor tRNA in the presence of the pyridinyl-amino tetrazine, GFP is detected, thereby indicating that the RS variant is specific for the amber codon and the pyridinyl-amino tetrazine. If the RS variant is unable to charge the suppressor tRNA in the presence of the pyridinyl-amino tetrazine, functional GFP protein is not translated due to the premature stop codon inserted into the GFP reporter gene. Moreover, if the RS variant can charge the suppressor tRNA in the absence of the non-natural amino acid, the variant is not specific for the nnAA. See, e.g., Examples and Takimoto et al., Molecular Biosystems, 5:931-934 (2009). In other instances, the selection marker can be a resistance gene containing an amber stop codon in the gene, such that in the presence of a selection agent (e.g., antibiotic, antibody, nutrient, and the like), cells contain a RS variant effective at codon suppression can be distinguished from those without an functional RS variant.

D. Introducing Suppressor Codons into Polynucleotides Encoding Proteins of Interest.

Once the desired aaRS protein is obtained, it is necessary to generate a target polynucleotide encoding a target protein with a desired site for the pyridinyl-amino tetrazine. Provided herein are methods for introducing a suppressor codon (e.g., amber TAG, ochre TAA, opal TGA) that is recognized by the RS variant described herein into the polynucleotide encoding a protein of interest. Non-limiting examples of a protein of interest include an antibody, antibody fragment, anti-idiotype antibody, chimeric antibody, humanized antibody, antibody fusion protein, secreted protein (e.g., hormone), transmembrane protein (e.g., receptor), enzyme, proprotein, protein fragment, pharmaceutically active protein, and a protein having potential industrial or therapeutic value. In some embodiments, the protein of interest is an antibody or an antibody fragment.

The coding region of the polynucleotide can be mutated to introduce a suppressor codon, e.g., an amber codon TAG into the open reading frame of the polynucleotide encoding the protein of interest such that the RS variant described herein can selectively suppress the introduced codon during translation and generate the protein of interest containing a non-natural amino acid at a desired location. The mutation can be introduced to avoid changing the open reading frame of the protein. For example, the polynucleotide encoding the protein of interest is mutated to insert a suppressor codon into the coding region of the protein in a selected position, such that the protein of interest contains the non-natural amino acid and is produced with the aid of the RS variant/suppressor tRNA pair. The position of the suppressor codon can be selected according to the primary, secondary, tertiary or quarternary structure of the protein, the function of the protein, the non-amino acid to be incorporated into the protein, and/or the biologically active adduct to be conjugated to the protein.

Methods for introducing a suppressor codon into the polynucleotide encoding the protein of interest include, but are not limited to, standard molecular biology techniques such as PCR, cloning and mutagenesis. As described above, useful mutagenesis techniques include, but are not limited to, site-directed mutagenesis (e.g., QuikchangeII™ Site Directed Mutagenesis kit, Agilent Technologies), random mutagenesis (Diversify™ PCR Random Mutagenesis Kit, Clontech), homologous recombinations, oligonucleotide-directed mutagenesis (e.g., Transformer™ Kit, Clontech), phosphorothioate-modified DNA mutagenesis, etc., can be used to generate amino acid substitutions, etc., can be used to generate amino acid substitutions. Other mutagenesis techniques are described above.

The mutated polynucleotide containing the suppressor codon can be cloned into an expression vector such as a plasmid, phage, phagemid, cosmid, bacteriophage, baculovirus vector, yeast plasmid, and the like. The expression vector can include the nucleic acid of the present invention that is operably linked to a promoter. Subsequently, the expression vector is introduced into a host cell to express the modified protein of interest. Any other vector may be used as long as it is replicable and viable in the host cell. The host cell can be a bacterial cell, an archaeal cell, a fungal cell, a yeast cell, an insect cell, or a mammalian cell.

The mutated polynucleotide encoding the protein of interest can be used a in a cell-free protein synthesis (CFPS) reaction for producing the protein of interest with a site-specific pyridinyl-amino tetrazine.

E. Cell Free Protein Synthesis (CFPS) of Pyridinyl-Amino Tetrazine-Containing Proteins.

After generating both the desired RS variant and the target polynucleotide encoding a target protein with a desired site for the pyridinyl-amino tetrazine amino acid, it is possible to synthesize the pyridinyl-amino tetrazine-containing target protein. Provided herein are methods of cell free protein synthesis for incorporating pyridinyl-amino tetrazine amino acid into the protein of interest. In particular, the CFPS reaction includes the compound of Formula I or the compound of Formula II in a concentration sufficient to permit selective incorporation of the selected pyridinyl-amino tetrazine into the protein of interest, a polynucleotide having a coding region encoding the protein of interest and including a suppression codon selectively positioned within its coding region, a tRNA able to be charged with the non-natural amino acid and complementary to the suppression codon of the protein of interest, and the RS variant provided herein.

In some embodiments, the amount of purified $M.$ $jannaschii$ RS variant protein in a CFPS reaction is in excess. The amount of purified $M.$ $jannaschii$ RS variant protein in the CFPS reaction can be in the range of about 1 µM to about 10 µM, e.g., 1 µM, 2 µM, 3 µM, 4 µM, 5 µM, 6 µM, 7 µM, 8 µM, 9 µM or 10 µM.

In some instances, the amount of RS variant protein used is in excess of the amount needed to aminoacylate the orthogonal amber suppressor tRNA. The amount of RS variant protein in the CFPS reaction can be in the range of about 1 µM to about 10 µM, e.g., 1 µM, 2 µM, 3 µM, 4 µM, 5 µM, 6 µM, 7 µM, 8 µM, 9 µM or 10 µM.

The amount of (S)-2-amino-3-(5-((6-methyl-1,2,4,5-tetrazin-3-ylamino)methyl)pyridin-2-yl)propanoic acid (e.g., the compound of Formula I) in the CFPS reaction can be in the range of about 1 mM to about 10 mM, e.g., 1 mM, 2 mM, 3 mM, 4 mM, 5 mM, 6 mM, 7 mM, 8 mM, 9 mM or 10 mM.

The amount of (S)-2-amino-3-(5-(6-methyl-1,2,4,5-tetrazin-3-ylamino)pyridin-3-yl)propanoic acid (e.g., the compound of Formula II) in the CFPS reaction can be in the range of about 1 mM to about 10 mM, e.g., 1 mM, 2 mM, 3 mM, 4 mM, 5 mM, 6 mM, 7 mM, 8 mM, 9 mM or 10 mM.

Cell free protein synthetic reaction systems are well-known in the art, and have been described in, e.g., Zawada et al., 2011, $Biotechnol.$ $Bioeng.,$ 108(7):1570-1578; Shimizu et al., $Nature$ $Biotechnology,$ 2001, 19:751-755; and U.S. Pat. Nos. 7,338,789, 8,183,010, 8,357,529 and 8,492,115, the disclosures of which are hereby incorporated by reference in their entirety for all purposes.

Cell free protein synthesis (CFPS) systems utilize cell extracts to support the synthesis of proteins in vitro from purified mRNA transcripts or from mRNA transcribed from DNA during the in vitro synthesis reaction. The reaction mixture is capable of catalyzing the synthesis of polypeptides from a nucleic acid template. The mixture includes one or more bacterial extracts and/or defined reagents. Exemplary bacterial extracts include, but are not limited to, $E.$ $coli$ S30 extracts, OmpT sensitive RF-1 attenuated $E.$ $coli$ extract, and variants thereof. The bacterial cells of the extract can overexpress a component of the CFPS system such as enzymes, e.g., DsbA, PpiA, FkpA, DegP and SlyD, and tRNAs (e.g., an orthogonal suppressor-encoding tRNA such as an orthogonal CUA-encoding tRNA).

Methods of preparing a cell extract for CFPS are described in, e.g., Zawada, J. "Preparation and Testing of $E.$ $coli$ S30 In Vitro Transcription Translation Extracts", Douthwaite, J. A. and Jackson, R. H. (eds.), $Ribosome$ $Display$ $and$ $Related$ $Technologies:$ $Methods$ $and$ $Protocols,$ $Methods$ $in$ $Molecular$ $Biology,$ vol. 805, pp. 31-41 (Humana Press, 2012); Jewett et al., $Molecular$ $Systems$ $Biology:$ 4, 1-10 (2008); Shin J. and Norieaux V., $J.$ $Biol.$ $Eng.,$ 4:8 (2010). Briefly, a bacterial culture is grown and harvested; suspended in an appropriate buffer (e.g., S30 buffer), and homogenized to lyse the cells.

The reaction mix of the CFPS system can also include at least ATP or an energy source; a template for production of the macromolecule, e.g., DNA, mRNA, etc.; amino acids and a non-natural amino acid, and such co-factors, enzymes and other reagents that are necessary for synthesis of the protein of interest, e.g., ribosomes, tRNAs (including orthogonal suppressor-encoding tRNA), polymerases, transcriptional factors, aminoacyl synthetases (e.g., RS variant provided herein), chaperones, elongation factors, initiation factors, etc.

When the suppressor codon is an amber codon, it is useful for the reaction mixture to include a component that can attenuate release factor (RF) activity or has decreased activity, e.g., a RF-1, RF-2 or RF-3 mutant. It is recognized by one skilled in the art that suppression efficiency of the amber suppressor tRNA is dependent on competition with the release factor 1 (RF1) for decoding the amber codon by the ribosome. RF1 acts to terminate the polypeptide chain at the stop codon, while the amber suppressor tRNA competes with RF1 to incorporate the non-natural amino acid during protein synthesis. Thus, decreasing the amount or activity of RF1 in the CFPS system can increase the suppression efficiency of the charged suppressor tRNAs. RF1 activity can be manipulated by using, e.g., RF1 inhibitory aptamers, antibodies against RF1, and RF-1 depleted cell lysates. In some instances, RF1 is omitted from the CFPS system.

The CFPS system can include an energy source such as a homeostatic energy source. Also included may be enzyme(s) that catalyze the regeneration of ATP from high-energy phosphate bonds, e.g., acetate kinase, creatine kinase, etc., via oxidative phosphorylation. Such enzymes may be present in the extracts used for translation, or may be added to the reaction mix. Optionally, a compound such as nicotinamide adenine dinucleotide (NADH), NAD$^+$ or acetyl-coenzyme A can be added for activation of oxidative phosphorylation.

To synthesize a protein of interest in vitro, a CFPS extract at some point comprises a mRNA molecule that encodes the protein of interest and contains a selectively positioned suppression codon (e.g., an amber codon). In some CFPS systems, mRNA is added exogenously after being purified from natural sources or prepared synthetically in vitro from cloned DNA using RNA polymerases such as RNA polymerase II, SP6 RNA polymerase, T3 RNA polymerase, T7 RNA polymerase, RNA polymerase III and/or phage derived RNA polymerases. In other systems, the mRNA is produced in vitro from a template DNA polynucleotide; both transcription and translation occur in this type of CFPS reaction. The template DNA contains a suppression codon selectively positioned with in the coding region. In yet other systems, transcription and translation systems are coupled or complementary transcription and translation systems, which carry out the synthesis of both RNA and the protein of interest in the same reaction, have been developed. In such in vitro transcription and translation systems, the CFPS extracts contain all the components (exogenous or endogenous) necessary both for transcription (to produce mRNA) and for translation (to synthesize the protein of interest) in a single system.

In some embodiments, the CFPS reaction is performed using the Cytomim™ system comprising NTPs, E. coli tRNAs and an orthogonal suppressor-encoding tRNA, amino acids and the specific non-natural amino acid (e.g., the compound of Formula I or Formula II), Mg$^{2+}$ acetate, Mg$^{2+}$ glutamate, K$^+$ acetate, K$^+$ glutamate, folinic acid, Tris pH 8.2, DTT, pyruvate kinase, T7 RNA polymerase, disulfide isomerase, sodium pyruvate, NAD, CoA, Na$^+$ oxalate, putrescine, spermidine, and bacterial extract. In some embodiments, the energy substrate for the Cytomim™ system is pyruvate, glutamic acid, and/or glucose. In some embodiments of the system, the nucleoside triphosphates (NTPs) are replaced with nucleoside monophosphates (NMPs).

In some embodiments, the CFPS reaction is performed using the PANOx-SP system comprising NTPs, tRNAs and an orthogonal suppressor-encoding tRNA, amino acids and the specific non-natural amino acid (e.g., the compound of Formula I or Formula II), Mg$^{2+}$ acetate, Mg$^{2+}$ glutamate, K$^+$ acetate, K$^+$ glutamate, folinic acid, Tris pH 8.2, DTT, pyruvate kinase, T7 RNA polymerase, disulfide isomerase, phosphoenol pyruvate (PEP), NAD, CoA, Na$^+$ oxalate, putrescine, spermidine, and an S30 extract.

To incorporate a pyridinyl-amino tetrazine amino acid into a protein of interest, the CFPS system includes the M. jannaschii RS variant protein of the present invention, a tRNA able to be charged with the pyridinyl-amino tetrazine amino acid and complementary to the suppression codon of the protein of interest, a polynucleotide having a coding region encoding the protein of interest and harboring a suppressor codon (e.g., amber codon) selectively positioned within the coding region, and the pyridinyl-amino tetrazine amino acid (e.g., the compound of Formula I or Formula II). The non-natural amino acid can be synthetic or derived from another biological source. For instance, the pyridinyl-amino tetrazine amino acid can be synthesized according to the method described in Example 1.

The protein of interest bearing the non-natural amino acid can be purified according to standard methods known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., PROTEIN PURIFICATION, J. C. Janson and Lars Ryden, eds., VCH Publishers, New York, 1989) to obtain substantially pure polypeptides.

The incorporation of the pyridinyl-amino tetrazine amino acid residue can be determined by methods such as, mass spectometry, protein sequencing, amino acid tagging such as by fluorescence, radioactivity, ELISA or other antibody screening assays, functional assays, or other methods known to one skilled in the art.

In some embodiments, the method further includes the step of conjugating a biologically active adduct to the specific non-natural amino acid of the protein of interest. In some instances, the conjugation is by a reaction between the tetrazine of the protein of interest and the trans-cyclooctene or the methylcyclopropene on the biologically active adduct.

F. Conjugation Chemistry for Pyridinyl-Amino Tetrazine-Containing Proteins.

Having the target protein containing the pyridinyl-amino tetrazine amino acid at the desired amino acid location, a biologically active adduct can be conjugated to the pyridinyl-amino tetrazine amino acid using a chemical reaction. Pyridyl tetrazine with in the protein can be conjugated to a biologically active adduct containing a dienophile using inverse electron demand Diels-Alder chemistry. This chemistry involves a cycloaddition between the electron-poor tetrazine moiety, serving as a diene, and an appropriate electron-rich dienophile. Such dienophiles can include strained and/or cyclic alkenes and alkynes, for example trans-cyclooctenes, cyclopropenes, and norbornenes. Upon reaction, the tetrazine and dienophile become covalently linked through an expanded or bridged ring structure. In turn, the biologically active adduct containing the dienophile become covalently linked to the protein of interest through its incorporated non-natural amino acid. For instance, the tetrazine-containing protein is purified by standard procedures, and then the purified protein is subject to a inverse electron demand Diels-Alder reaction to directly conjugate a trans-cyclooctene or a methylcyclopropene on a biologically active adduct to the tetrazine of the protein.

Exemplary biologically active adducts for use in the present invention include, not are not limited to, small molecules, oligonucleotides, peptides, amino acids, nucleic acids, sugars, oligosaccharides, polymers, synthetic polymers, chelators, fluorophores, chromophores, other detectable agents, drug moieties, cytotoxic agents, detectable agents, and the like.

Methods for conjugating proteins to various biologically active adducts through tetrazine moieties are reviewed in, e.g., Šečkutė and Devaraj, Curr. Opin. Chem. Biol. 2013, 17:1-7. Others have reported reactions between tetrazine moieties and particular dienophiles, such as norbornenes (Devaraj et al., Bioconjugate Chem. 2008, 19: 2297-2299), trans-cyclooctenes (Lang et al., J. Am. Chem. Soc. 2012, 134: 10317-20320; Devaraj et al., Angew. Chem. Int. Ed. 2010, 49: 2869-2872), and cyclopropenes, e.g., substituted cyclopropenes such as methylcyclopropene (Yu et al., Angew. Chem. Int. Ed. 2012, 51: 10600-10604; Patterson et al., J. Am. Chem. Soc. 2012, 134: 18638-18643), as well as biological applications of these reactions. The reactions are examples of inverse electron demand Diels-Alder chemistry and can occur efficiently in aqueous solution and under conditions that allow proteins to remain folded, competent to bind substrates, and/or enzymatically active. In some cases, Diels-Alder reactions involving tetrazine moieties can occur in vivo or be triggered by light.

Useful chemical moieties on the dienophile include those that can be reacted with the pyridyl tetrazine amino acid within the protein of interest. Such chemical groups can include, for example and without limitation, hydroxyl, carboxyl, carbonyl, formyl, sulfonic, sulfhydryl, amino, azido, alkyl, alkenyl, alkynyl, phenyl, or aromatic groups, or combinations thereof. Chemical moieties are chosen that do not interfere with the Diels-Alder conjugation chemistry.

The conjugated protein of interest can be purified according to standard methods known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., PROTEIN PURIFICATION, J. C. Janson and Lars Ryden, editors, VCH Publishers, New York, 1989) to obtain substantially pure polypeptides.

The conjugated protein of interest can be quantitated according to standard methods known in the art including, but not limited to, microfluidic electrophoresis, gel electrophoresis, western blotting, immunoassays (e.g., ELISA), and other assays to assess the activity of the conjugated protein.

III. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. Synthesizing Pyridinyl-Amino Tetrazine Amino Acids

The pyridinyl-amino tetrazine amino acids can be synthetic or derived from another biological source. This example provides a method of preparing the compound of Formula II. The chemical reaction is shown below.

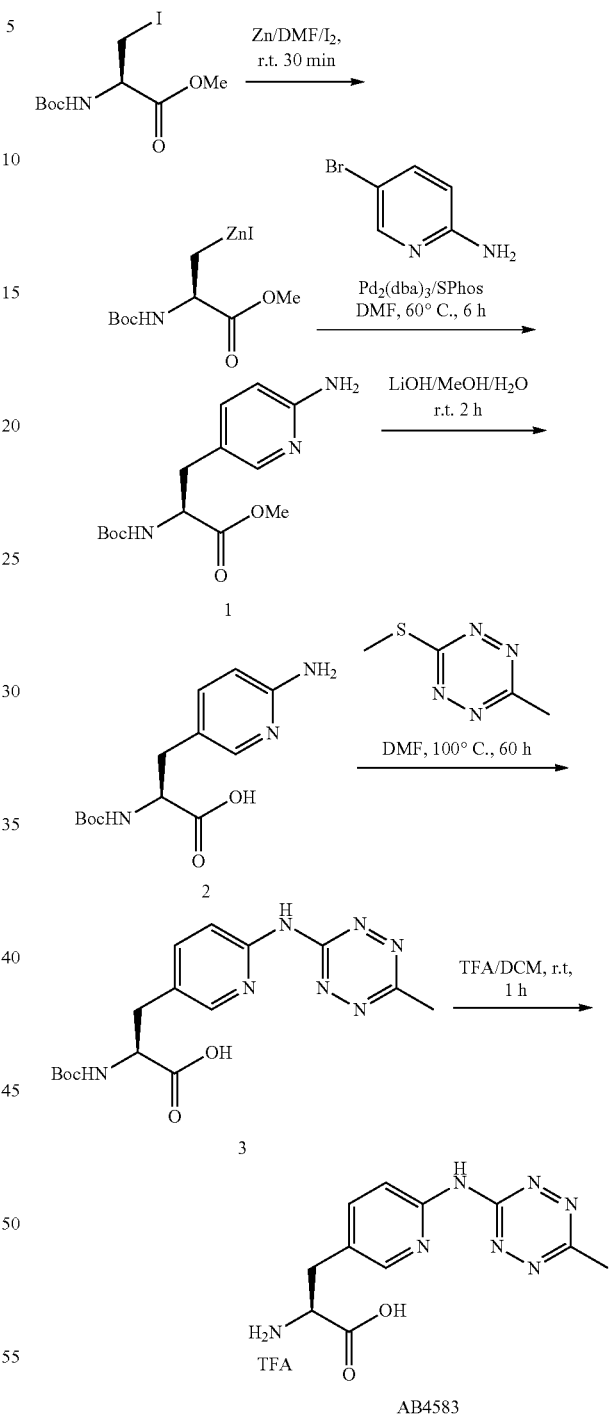

Preparation of compound 1. Iodine (400 mg, 1.08 mmol, 0.15 eq) was added to a suspension of zinc powder (1.37 g, 21 mmol, 2.0 eq) in DMF at room temperature (RT) under $N_2$. The suspension was stirred at RT for about 10 min while the color changed from brown to grey. Carbamic acid, N-(3-iodopropyl)-1,1-dimethylethyl ester (3.45 g, 10.5 mmol, 1.0 eq) and iodine (400 mg, 1.08 mmol, 0.15 eq) was added to the suspension. The reaction mixture was stirred at RT for 30 min (heat produced from the reaction can be observed) and cooled to RT to give a crude zinc reagent, which was used for next step without further purification.

Anhydrous DMF (5 mL) under $N_2$ was added to a mixture of the 2-aminyl-5-bromopyridine (2.2 g, 12.6 mmol, 1.2 eq), $Pd_2(dba)_3$ (292 mg, 0.318 mmol, 0.025 eq) and ligand SPhos (0.52 g, 1.27 mmo, 0.1 eq) in a Schlenk tube. The mixture was stirred at RT for 5 min. The zinc reagent (1.0 eq) suspension prepared above was added into the mixture under $N_2$. The reaction was heated to 60° C. for 6 h. It was then cooled to RT and filtered through a pad of Celite. Next, the filtrate was concentrated and purified by silica gel column (DCM:MeOH=9:1) to give compound 1 and 2-aminyl-5-bromopyridine.

Preparation of compound 2. Aqueous LiOH (800 mg, 19 mmol, 5.0 eq, in 10 mL of water) in a mixed solvent of THF (5 mL) and MeOH (10 mL) was added to a mixture of compound 1 (containing 2-aminyl-5-bromopyridine). Then, the mixture was stirred at RT for 2 h. Next, the solvent was removed and the residue was purified by silica gel column (DCM:MeOH:Et$_3$N, 9:1:1) to give product 2 (1.4 g, 37% two-steps) as a triethylamine salt.

Preparation of compound 3. 4-methyltetrazine methyl sulfide (1.56 g, 11.0 mmol, 3.0 eq) was added the triethylamine salt of 2 (1.4 g, 3.66 mmol, 1.0 eq) in DMF (10.0 mL) in a sealed tube. Next, the tube was heated to 100° C. for 60 h. The reaction mixture was then cooled and purified by prep-HPLC to give product 3 (480 mg, 35%).

Preparation of compound 3. Compound 3 (190 mg, 0.51 mmol) was dissolved in 20% TFA in DCM (8 mL) and stirred at RT for 1 h. The solvent was removed under reduced pressure, and the residue was re-dissolved in water, frozen and lyophilized to give the compound of Formula II (240 mg, 78%, TFA salts) as a red solid.

The compound of Formula I was synthesized using the same method as described above with the modification of starting with the appropriate compound 1 to synthesize (S)-2-amino-3-(5-(((6-methyl-1,2,4,5-tetrazin-3-ylamino)methyl)pyridin-2-yl)propanoic acid.

Example 2. Generating Pyridyl-Amino Tetrazine Specific TyrRS Variants and Determining Suppression Efficiency This example provides a method for using pyridyl-amino tetrazine specific TyrRS variants in cell free protein synthesis. A detailed description of the method is found in, for example, Zimmerman et al., *Bioconjugate Chemistry*, 2014, 25, 351-361, which is hereby incorporated by reference in its entirety for all purposes. The example also illustrates a method of assessing the activity and specificity of pyridyl-tetrazine-specific RS variants in a GFP-based amber suppression efficiency assay. The RS variants tested are provided in Table 1, which shows the amino acid substitutions of the variants relative to wild-type *M. jannaschii* tyrosyl tRNA synthetase set forth in SEQ ID NO: 1.

TABLE 1

RS variants with amino acid substitutions to wild-type TyrRS.

| Pyridyl-tetrazine amino acid | TyrRS variant clone | Y32 | L65 | H70 | F108 | Q109 | D158 | I159 | L162 |
|---|---|---|---|---|---|---|---|---|---|
| Formula I  | 1A7 | L | V | A | W | S | V | A | S |
| Formula I  | 2A2 | L | V | A | W | S | V | A | V |
| Formula II | 1B7 | G | A | A | P | Q | G | I | S |
| Formula II | 1B8 | G | V | H | P | Q | G | I | S |
| Formula II | 2A1 | G | V | A | W | Q | G | I | S |
| Formula II | 2B7 | G | A | A | P | H | G | I | S |
| Formula II | 2B5 | G | A | A | P | Q | G | I | S |
| Formula II | 2A5 | G | A | A | F | S | G | I | S |
| Formula II | 2B4 | G | A | A | W | S | G | A | S |
| Formula II | 2B3 | G | V | A | W | S | G | A | G |
| Formula II | 2A9 | G | V | A | F | S | G | I | S |

Y32, L65, H70, F108, Q109, D158, I159 and L162 represent the wild-type amino acid residues in the specified amino acid positions of wild-type *M. jannasschii* TyrRS.

The RS variants described herein were used to incorporate the compound of Formula I or the compound Formula II into the reporter protein Superfolder GFP. GFP containing a TAG stop codon at position 49 (GFP (K49TAG)) was expressed in a cell-free protein synthesis reaction as described in Zawada et al., 2011, *Biotechnol. Bioeng.*, 108(7)1570-1578 with the following modifications. The cell free extracts were prepared from an OmpT sensitive RF-1 attenuated strainthat was also engineered to overexpress *E. coli* DsbC, and a similar RF-1 attenuated *E. coli* strain that was engineered to produce an orthogonal CUA-encoding tRNA for insertion of a non-natural amino acid at an amber stop codon. The cell free extracts were blended (at a ratio of 85:15), and then added to a premix containing all other components of a cell-free protein synthesis system except for DNA encoding GFP (K49TAG). The final concentration in the cell-free protein synthesis reaction was 30% cell extract, with or without 2 mM non-natural amino acid (either Formula I or Formula II), 4 µM, 2 µM, 1 µM or no nnAA-specific RS variant (e.g., variant clone 1A7, 2A2, 1B7, 1B8, 2A1, 2B7, 2B5, 2A5, 2B4, 2B3, or 2A9), 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 0.5 mM for tyrosine and phenylalanine), 4 mM sodium oxalate, 1 mM putrescine, 1.5 mM spermidine, 15 mM potassium phosphate, 100 nM T7 RNAP, 10 µg/mL GFP (K49TAG) expression template plasmid. The cell-free synthesis reactions were initiated by the addition of the plasmid DNA encoding GFP (K49TAG). The reactions were incubated at 30° C. for 12 h on a shaker at 650 rpm. After 12 hours of expression at the end point GFP fluorescence signal was measured at excitation at 476 nm, emission at 510 nm on a SpectraMax M5 fluorescence plate reader.

Clone 2A2, specific for Formula I, was titrated into the CFPS reactions expressing GFP with an amber stop codon at position 49 (GFP K49TAG) in the absence or presence of 4 μM Formula I. Full-length GFP was expressed only in the presence of the compound of Formula I and its-specific aaRS through suppression of the TAG codon via incorporation of the compound. GFP levels from the reaction containing the compound of Formula I were comparable to those of GFP, without a premature TGA codon, expressed in in a comparable CFPS reaction (the positive GFP control reaction). FIG. 1 shows the GFP expression produced by clone 2A2 in the absence or presence of 4 mM Formula I during cell-free protein synthesis.

Figure 2:
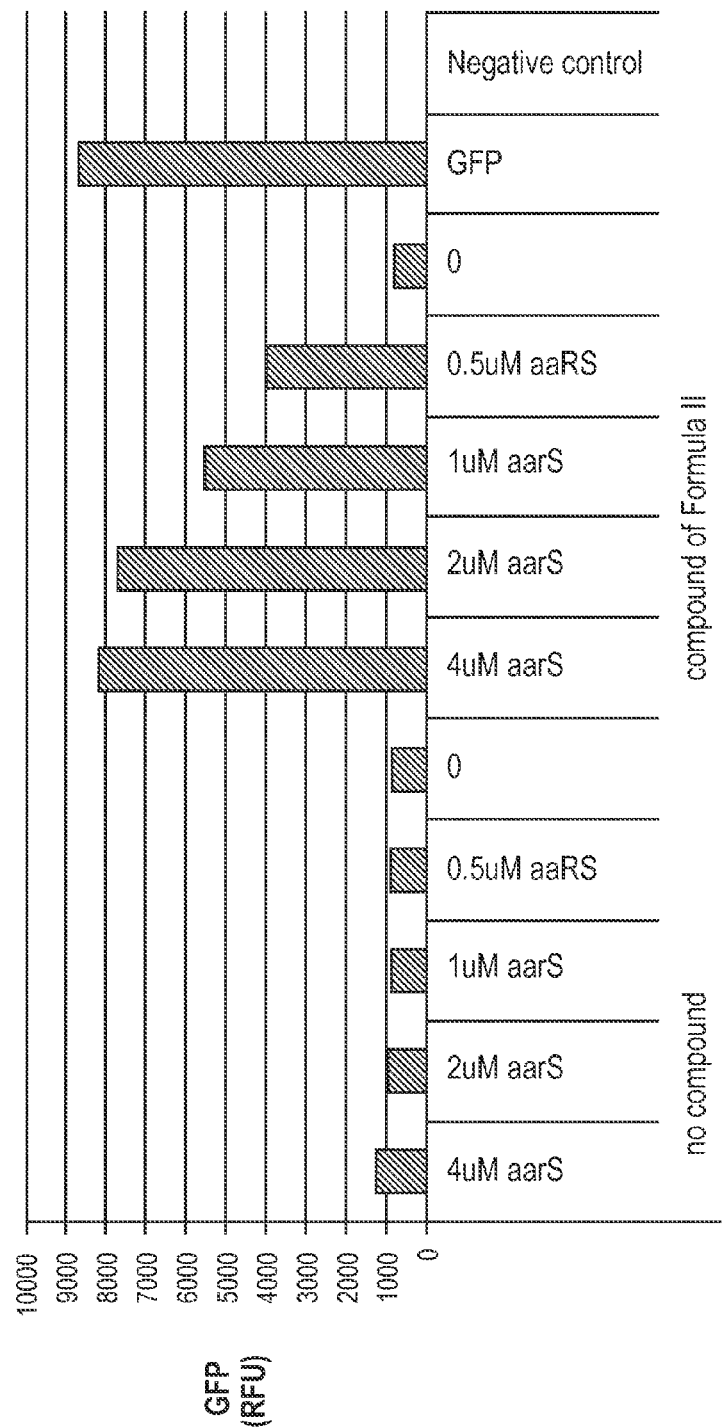
FIG. 2 shows GFP expression in the CFPS based GFP K49TAG amber suppression assay for the 2A9 variant which contains the following amino acid substitutions relative to SEQ ID NO:1: Y32G, L65V, H70A, Q109S, D158G, and L162S. The assay measures GFP expression in the presence and absence of the non-natural amino acid of Formula II.

Similarly, clone 2A9, specific for Formula II, was titrated into the GFP-based amber supression CFPS reactions in the absence or presence of 4 μM Formula II. Full-length GFP was expressed only in the presence of the compound of Formula II and its-specific aaRS through suppression of the TAG codon via incorporation of the compound. Levels of GFP from the reaction containing the compound of Formula II were comparable to those of the positive GFP control reaction. FIG. 2 shows the GFP expression produced by clone 2A9 in the absence or presence of 1 mM Formula II during cell-free protein synthesis.

The synthetase variants showed a high degree of GFP amber suppression only in the presence of pyridyl-tetrazine amino acid. The variants tested had high activity for the non-natural amino acids, while discriminating against the 20 common natural amino acids. The RS variants 2A2 and 2A9 had high amber suppression efficiencies (e.g., high levels of GFP detected) in the presence of the pyridyl-amino tetrazine compounds of Formula I and II, respectively, and substantially no amber supression (e.g., non-specific background levels of GFP detected) in the reactions lacking the non-natural amino acid and containing the common naturally occurring amino acids (FIG. 1).

In summary, this example shows that several RS mutant proteins (e.g., muteins) can be used for site-specific incorporation of Formula I or Formula II with high translational fidelity into proteins in response to the amber codon, TAG.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A composition comprising an aminoacyl-tRNA synthetase (RS) wherein the RS:

i) preferentially aminoacylates to a degree of greater than 90% a tRNA with (S)-2-amino-3-(5-(6-methyl-1,2,4,5-tetrazin-3-ylamino)pyridin-3-yl)propanoic acid or a compound having the formula:

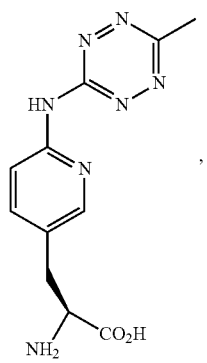

II compared to the 20 common naturally occurring amino acids;

ii) has a sequence identity of over 80% to *Methanococcus jannaschii* tyrosyl tRNA synthetase (TyrRS) having SEQ ID NO: 1; and iii) using SEQ ID NO: 1 as a reference sequence, has:
  a) at position Y32 amino acid: G;
  b) at position L65 amino acid: V or A;
  c) at position H70 amino acid: A or H
  d) at position F108 amino acid: P, F or W;
  e) at position Q109 amino acid: Q, H or S;
  f) at position D158 amino acid: G;
  g) at position I159 amino acid: I or A; and
  h) at position L162 amino acid: S or G.

2. The composition of claim 1, wherein the RS:
a) has the amino acid substitution L65A or L65V
b) has a sequence identity of at least least 90% of SEQ ID NO: 1, or
c) is selected from the group of amino acid sequences consisting of SEQ ID NOS: 4 and 5.

3. A polynucleotide encoding the aminoacyl-tRNA synthetase (RS) of claim 1.

4. The polynucleotide of claim 3 encoding the RS, wherein the RS
a) has the amino acid substitution L65A or L162V;
b) has a sequence identity of at least least 90% of SEQ ID NO: 1; or
c) is selected from the group of amino acid sequences consisting of SEQ ID NOS: 4 and 5.

5. A cell free protein synthesis system for selectively incorporating (S)-2-amino-3-(5-(6-methyl-1,2,4,5-tetrazin-3-ylamino)pyridin-3-yl)propanoic acid or a compound having the formula:

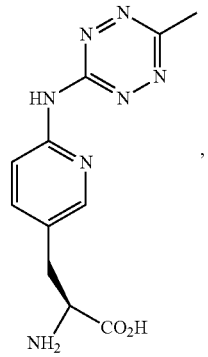

II into a protein of interest, the system comprising:
a) a cell free extract of bacteria having biologically functioning tRNA, amino acids and ribosomes necessary for cell free protein synthesis;
b) a polynucleotide having a coding region encoding the protein of interest and including a suppression codon selectively positioned within its coding region;
c) the compound of Formula II in a concentration sufficient to permit selective incorporation of the compound of Formula II into the protein of interest;
d) a tRNA able to be charged with the compound of formula II and complementary to the suppression codon of the protein of interest; and
e) the aminoacyl-tRNA synthetase (RS) of claim 1.

6. The cell free protein synthesis system of claim 5, wherein the cell free extract has an active oxidative phosphorylation system.

7. The cell free protein synthesis system of claim 5, wherein the protein of interest is an antibody or antibody fragment.

8. A method for selectively incorporating (S)-2-amino-3-(5-(6-methyl-1,2,4,5-tetrazin-3-ylamino)pyridin-3-yl)propanoic acid or a compound having the formula:

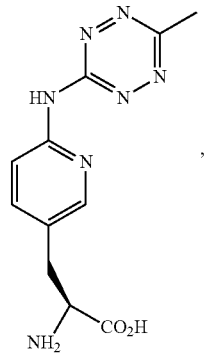

II into a protein of interest, the method comprising the steps of:
a) combining a cell free extract of bacteria having containing biologically functioning tRNA, amino acids and ribosomes necessary for cell free protein synthesis with the following reagents:
  i) a polynucleotide having a coding region encoding the protein of interest and including a suppression codon selectively positioned within its coding region;

ii) the compound of Formula II in a concentration sufficient to permit selective incorporation of the compound of Formula II into the protein of interest;
iii) a tRNA able to be charged with the compound of formula II and complementary to the suppression codon of the protein of interest; and
iv) an aminoacyl-tRNA synthetase (RS) wherein the RS:

preferentially aminoacylates to a degree of greater than 90% a tRNA with the compound of Formula II compared to the 20 common naturally occurring amino acids;

has a sequence identity of over 80% to *Methanococcus jannaschii* tyrosyl tRNA synthetase (TyrRS) having SEQ ID NO: 1; and using SEQ ID NO: 1 as a reference sequence, has:
a) at position Y32 amino acid: G;
b) at position L65 amino acid: V or A;
c) at postion H70 amino acid: A or H
d) at position F108 amino acid: P, F or W;
e) at position Q109 amino acid: Q, H or S;
f) at position D158 amino acid: G;
g) at position I159 amino acid: I or A; and
h) at position L162 amino acid: S or G; and b) incubating the combination of step (a) under conditions permitting selective incorporation of the compound of Formula II into the protein of interest.

9. The method of claim 8, further comprising the step of conjugating a biologically active adduct to the compound of Formula II within the protein of interest.

10. The method of claim 9, wherein the conjugation is by an inverse electron demand Diels-Alder reaction between the tetrazine of the protein of interest and a trans-cyclooctene on a biologically active adduct or by an inverse electron demand Diels-Alder reaction between the tetrazine of the protein of interest and a methylcyclopropene on a biologically active adduct.

* * * * *

UNITED STATES PATENT AND TRADEMARK OFFICE
CERTIFICATE OF CORRECTION

PATENT NO. : 9,988,619 B2
APPLICATION NO. : 15/028379
DATED : June 5, 2018
INVENTOR(S) : Erik S. Zimmerman and Christopher Thanos Page 1 of 1

It is certified that error appears in the above-identified patent and that said Letters Patent is hereby corrected as shown below:

In Column 42:
Claim 8, Line 4, "1159" should be --I159--.

Signed and Sealed this
Seventh Day of August, 2018

Andrei Iancu
*Director of the United States Patent and Trademark Office*

SEQUENCE LISTING

```
<160> NUMBER OF SEQ ID NOS: 5

<210> SEQ ID NO 1
<211> LENGTH: 306
<212> TYPE: PRT
<213> ORGANISM: Methanococcus jannaschii
<220> FEATURE:
<223> OTHER INFORMATION: wild-type (WT) tyrosyl tRNA synthetase (TyrRS),
      reference sequence

<400> SEQUENCE: 1

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190
```

```
Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 2
<211> LENGTH: 306
<212> TYPE: PRT
<213> ORGANISM: Artificial Sequence
<220> FEATURE:
<223> OTHER INFORMATION: synthetic aminoacyl-tRNA synthetase (RS)
      variant

<400> SEQUENCE: 2

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Val Leu Ala Asp Leu Ala Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Trp Ser Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Val Ala His
145                 150                 155                 160

Tyr Ser Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240
```

```
Ile Met Glu Ile Ala Lys Tyr Phe Leu Glu Tyr Pro Leu Thr Ile Lys
            245                 250                 255

Arg Pro Glu Lys Phe Gly Gly Asp Leu Thr Val Asn Ser Tyr Glu Glu
        260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 3
<211> LENGTH: 306
<212> TYPE: PRT
<213> ORGANISM: Artificial Sequence
<220> FEATURE:
<223> OTHER INFORMATION: synthetic aminoacyl-tRNA synthetase (RS)
      variant

<400> SEQUENCE: 3

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Val Leu Ala Asp Leu Ala Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
            85                  90                  95

Gly Leu Lys Ala Lys Tyr Val Tyr Gly Ser Glu Trp Ser Leu Asp Lys
        100                 105                 110

Asp Tyr Thr Leu Asn Val Tyr Arg Leu Ala Leu Lys Thr Thr Leu Lys
    115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Val Ala His
145                 150                 155                 160

Tyr Val Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
```

275                 280                 285

Asn Ala Val Ala Glu Glu Leu Ile Lys Ile Leu Glu Pro Ile Arg Lys
    290                 295                 300

Arg Leu
305

<210> SEQ ID NO 4
<211> LENGTH: 306
<212> TYPE: PRT
<213> ORGANISM: Artificial Sequence
<220> FEATURE:
<223> OTHER INFORMATION: synthetic aminoacyl-tRNA synthetase (RS)
      variant

<400> SEQUENCE: 4

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Gly
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
    50                  55                  60

Ala Leu Ala Asp Leu Ala Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Ser Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Ile His
145                 150                 155                 160

Tyr Ser Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

```
<210> SEQ ID NO 5
<211> LENGTH: 306
<212> TYPE: PRT
<213> ORGANISM: Artificial Sequence
<220> FEATURE:
<223> OTHER INFORMATION: synthetic aminoacyl-tRNA synthetase (RS)
      variant

<400> SEQUENCE: 5

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Val Leu Ala Asp Leu Ala Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Ser Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Ile His
145                 150                 155                 160

Tyr Ser Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```